US00PP25486P2

(12) United States Plant Patent
Heiser

(10) Patent No.: US PP25,486 P2
(45) Date of Patent: Apr. 28, 2015

(54) ***PETUNIA* PLANT NAMED 'BHTUN6202'**

(50) Latin Name: *Petunia×hybrida*
Varietal Denomination: BHTUN6202

(71) Applicant: Brian Heiser, Escondido, CA (US)

(72) Inventor: Brian Heiser, Escondido, CA (US)

(73) Assignee: Plant 21 LLC, Bonsall, CA (US)

( * ) Notice: Subject to any disclaimer, the term of this patent is extended or adjusted under 35 U.S.C. 154(b) by 216 days.

(21) Appl. No.: 13/815,648

(22) Filed: Mar. 13, 2013

(51) Int. Cl.
*A01H 5/00* (2006.01)

(52) U.S. Cl.
USPC ..... Plt./356.21

(58) Field of Classification Search
USPC ..... Plt./356.21
See application file for complete search history.

*Primary Examiner* — Anne Grunberg

(57) ABSTRACT

A new and distinct cultivar of *Petunia* plant named 'BHTUN6202', characterized by its compact, outwardly spreading to trailing and low mounding plant habit; freely branching habit; vigorous growth habit; early and freely flowering habit; light red purple-colored flowers; and good garden performance.

1 Drawing Sheet

Botanical designation: *Petunia×hybrida.*
Cultivar denomination: 'BHTUN6202'.

BACKGROUND OF THE INVENTION

The present invention relates to a new and distinct cultivar of *Petunia* plant, botanically known as *Petunia×hybrida* and hereinafter referred to by the name 'BHTUN6202'.

The new *Petunia* plant is a product of a planned breeding program conducted by the Inventor in Bonsall, Calif. The objective of the breeding program is to create new freely-flowering and uniform *Petunia* plants with unique flower color and good garden performance.

The new *Petunia* plant originated from a cross-pollination made by the Inventor on Aug. 2, 2010 in Bonsall, Calif. of *Petunia×hybrida* 'USTUNI8902', disclosed in U.S. Plant Pat. No. 17,895, as the female, or seed, parent with *Petunia×hybrida* 'Asakura Roman', not patented, as the male, or pollen, parent. The new *Petunia* plant was discovered and selected by the Inventor as a single flowering plant within the progeny of the stated cross-pollination in a controlled environment in Bonsall, Calif. on May 12, 2011.

Asexual reproduction of the new *Petunia* plant by vegetative cuttings in a controlled greenhouse environment in Bonsall, Calif. since May 12, 2011, has shown that the unique features of this new *Petunia* plant are stable and reproduced true to type in successive generations.

SUMMARY OF THE INVENTION

Plants of the new *Petunia* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'BHTUN6202'. These characteristics in combination distinguish 'BHTUN6202' as a new and distinct *Petunia* plant:

1. Compact, outwardly spreading to trailing and low mounding plant habit.

2. Freely branching habit.
3. Vigorous growth habit.
4. Early and freely flowering habit.
5. Light red purple-colored flowers.
6. Good garden performance.

Plants of the new *Petunia* can be compared to plants of the female parent, 'USTUNI8902'. In side-by-side comparisons conducted in Bonsall, Calif., plants of the new *Petunia* differ primarily from plants of 'USTUNI8902' in the following characteristics:

1. Plants of the new *Petunia* have larger flowers than plants of 'USTUNI8902'.
2. Plants of the new *Petunia* and 'USTUNI8902' differ in flower color as plants of 'USTUNI8902' have darker red purple-colored flowers with less distinct venation.

Plants of the new *Petunia* can be compared to plants of the male parent, 'Asakura Roman'. In side-by-side comparisons conducted in Bonsall, Calif., plants of the new *Petunia* differ primarily from plants of 'Asakura Roman' in the following characteristics:

1. Plants of the new *Petunia* are more vigorous than plants of 'Asakura Roman'.
2. Plants of the new *Petunia* are more freely branching than plants of 'Asakura Roman'.
3. Plants of the new *Petunia* and 'Asakura Roman' differ in flower color as plants of 'Asakura Roman' have deep blue and pink bi-colored flowers.
2. Plants of the new *Petunia* and the male parent selection differ in flower color as plants of the male parent selection have pink-colored flowers.

Plants of the new *Petunia* can be compared to plants of 'USTUNI6001', disclosed in U.S. Plant Pat. No. 17,730. In side-by-side comparisons conducted in Bonsall, Calif., plants of the new *Petunia* differed primarily from plants of 'USTUNI6001' in the following characteristics:

1. Plants of the new *Petunia* were shorter than plants of 'USTUNI6001'.
2. Plants of the new *Petunia* and 'USTUNI6001' differed in flower color as plants of 'USTUNI6001' had bright pink-colored flowers with less distinct venation.

Plants of the new *Petunia* can also be compared to plants of 'USTUNI153', disclosed in U.S. Plant Pat. No. 14,856. In side-by-side comparisons, plants of the new *Petunia* differed primarily from plants of 'USTUNI153' in the following characteristics:

1. Plants of the new *Petunia* had smaller and darker green-colored leaves than plants of 'USTUNI153'.
2. Plants of the new *Petunia* had smaller flowers than plants of 'USTUNI153'.
3. Plants of the new *Petunia* and 'USTUNI153' differed in flower color as plants of 'USTUNI153' had darker-colored flowers.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the bottom of the sheet comprises a side perspective view of a typical plant of 'BHTUN6202' grown in a container.

The photograph at the top of the sheet is a close-up view of a typical flowering plant of 'BHTUN6202'.

DETAILED BOTANICAL DESCRIPTION

The aforementioned photographs and following observations, measurements and values describe plants grown during the late autumn in 15.24-cm containers in an outdoor nursery in Bonsall, Calif. During the production of the plants, day temperatures ranged from 18° C. to 38° C., night temperatures ranged from 9° C. to 18° C. and light levels ranged from 7,000 to 10,000 foot-candles. Plants were pinched one time and were three months old when the photographs and description were taken. In the following description, color references are made to The Royal Horticultural Society Colour Chart, 2007 Edition, except where general terms of ordinary dictionary significance are used.

Botanical classification: *Petunia×hybrida* 'BHTUN6202'.

Parentage:

*Female, or seed, parent.*—*Petunia×hybrida* 'USTUNI8902', disclosed in U.S. Plant Pat. No. 17,895.

*Male, or pollen, parent.*—*Petunia×hybrida* 'Asakura Roman', not patented.

Propagation:

*Type*.—Terminal vegetative cuttings.

*Time to produce a rooted young plant, summer*.—About 15 days at temperatures ranging from 16° C. to 29° C.

*Time to produce a rooted young plant, winter*.—About 20 days at temperatures ranging from 16° C. to 21° C.

*Root description*.—Medium in thickness, fibrous; white in color.

*Rooting habit*.—Freely branching; medium density.

Plant description:

*Plant and growth habit*.—Compact, outwardly spreading to trailing and low mounding plant habit with about four primary lateral branches with multiple secondary lateral branches developing per plant; dense and bushy appearance; pinching enhances development of lateral branches; vigorous growth habit.

*Plant height*.—About 11.8 cm.

*Plant diameter* (*area of spread*).—About 32 cm by 34 cm.

*Lateral branches*.—Length: About 19 cm. Diameter: About 2 mm. Internode length: About 1.7 cm. Aspect: Initially upright then falling outwardly. Texture: Pubescent. Color: Close to 144A.

Foliage description:

*Arrangement*.—Alternate before flowering; opposite after flowers develop; simple.

*Length*.—About 3.4 cm.

*Width*.—About 2.1 cm.

*Shape*.—Ovate.

*Apex*.—Acute.

*Base*.—Attenuate.

*Margin*.—Entire.

*Texture, upper and lower surfaces*.—Pubescent; glandular.

*Venation pattern*.—Pinnate, arcuate.

*Color*.—Developing leaves, upper surface: Close to 144A. Developing leaves, lower surface: Close to 146B. Fully expanded leaves, upper surface: Close to 146A; venation, close to 146B. Fully expanded leaves, lower surface: Close to 146B; venation, close to 146C.

*Petioles*.—Length: About 1.3 cm. Diameter: About 2 mm. Texture, upper and lower surfaces: Pubescent; glandular. Color, upper and lower surfaces: Close to 146C.

Flower description:

*Flower type and flowering habit*.—Single axillary salverform flowers; flowers face mostly upright; freely flowering habit with about eight to ten flowers developing per lateral branch and about 100 flowers developing per plant.

*Natural flowering season*.—Long day responsive; long flowering period, plants flower from early spring until frost in the autumn, flowering continuous during this period; early flowering habit, plants begin flowering about six weeks after planting.

*Flower longevity on the plant*.—About three to four days; flowers persistent.

*Fragrance*.—None detected.

*Flower buds*.—Length: About 3.8 cm. Diameter: About 7 mm. Shape: Oblong. Color: Close to 85C.

*Flower diameter*.—About 4.8 cm.

*Flower depth* (*height*).—About 4 cm.

*Throat diameter, distal*.—About 1.2 cm.

*Tube length*.—About 2.8 cm.

*Tube diameter, proximal*.—About 3 mm.

*Petals*.—Quantity and arrangement: Five petals fused in a single salverform whorl. Petal lobe length (from throat): About 2.2 cm. Petal lobe width: About 2.2 cm. Petal lobe shape: Obovate. Petal lobe apex: Nearly round to broadly acute. Petal lobe margin: Entire. Petal lobe texture, upper surface: Smooth, glabrous; velvety. Petal lobe texture, lower surface: Smooth, glabrous. Throat texture: Smooth, glabrous. Tube texture: Pubescent. Color: When opening, upper surface: Close to 70C. When opening, lower surface: Close to 73D. Fully opened, upper surface: Close to N74C; venation, close to 70B; color does not fade with development. Fully opened, lower surface: Close to 76C; venation, close to 194B to 194C. Flower throat (inside): Close to 76C; venation, close to 187C. Flower tube (outside): Close to 76A to 76B; venation, close to N186D.

*Sepals*.—Quantity and arrangement: Five sepals fused in a single star-shaped whorl. Length: About 1.8 cm. Width: About 4 mm. Shape: Lanceolate. Apex: Rounded to slightly acute. Margin: Entire. Texture, upper and lower surfaces: Pubescent; minute. Color, upper surface: Close to 146A. Color, lower surface: Close to 146B.

*Peduncles*.—Length: About 2.3 cm. Width: About 1 mm. Angle: About 45° from the stem axis. Strength: Strong. Texture: Pubescent; minute. Color: Close to 144A.

*Reproductive organs*.—Stamens: Quantity per flower: Five. Filament length: About 1.6 cm. Filament color: Close to 84D. Anther length: About 1.5 mm. Anther shape: Oval. Anther color: Close to 196D. Pollen amount: Moderate. Pollen color: Close to 202D. Pistils: Quantity per flower: One. Pistil length: About 2 cm. Style length: About 1.4 cm. Style color: Close to 194C. Stigma shape: Round. Stigma color: Close to 194A. Ovary color: Close to 146B.

*Seeds and fruits*.—Seed and fruit development has not been observed on plants of the new *Petunia*.

Pathogen & pest resistance: Plants of the new *Petunia* have not been noted to be resistant to pathogens or pests common to *Petunia* plants.

Garden performance: Plants of the new *Petunia* have been observed to have good garden performance and have been observed to tolerate rain, wind and temperatures ranging from about 1° C. to about 40° C.

It is claimed:

1. A new and distinct *Petunia* plant named 'BHTUN6202' as illustrated and described.

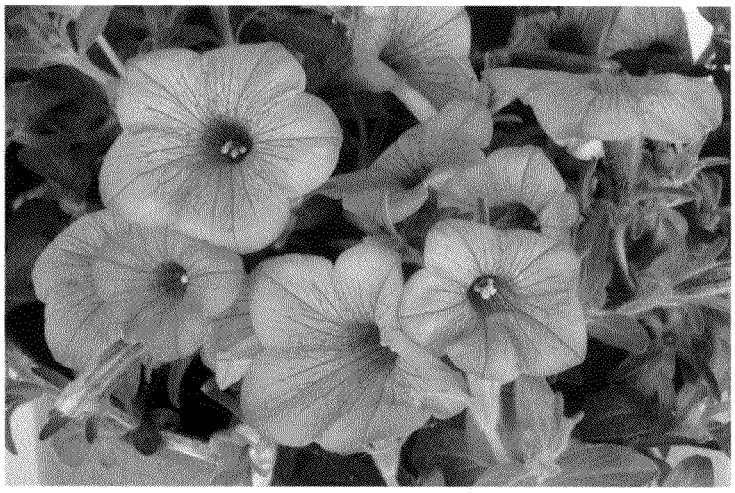
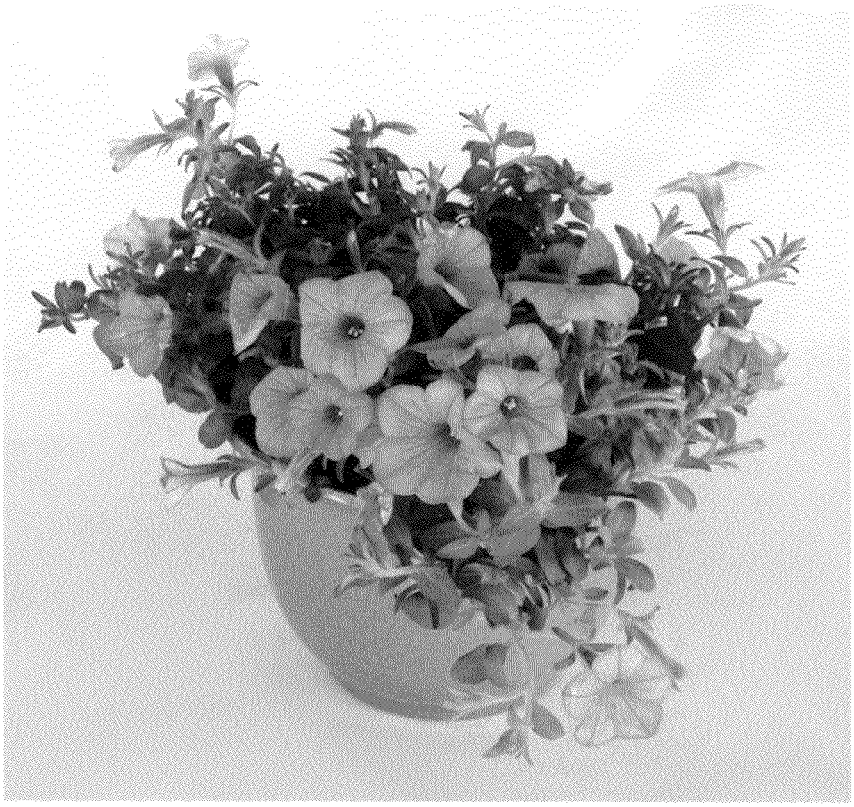

* * * * *